United States Patent [19]

Tamm

[11] 3,982,834
[45] Sept. 28, 1976

[54] DEVICE FOR ATOMIZATION OF A SAMPLE

[75] Inventor: Rolf Günther Arnold Tamm, Salem, Germany

[73] Assignee: Bodenseewerk Perkin-Elmer & Co. GmbH, Uberlingen, Germany

[22] Filed: Aug. 28, 1975

[21] Appl. No.: 608,514

Related U.S. Application Data

[63] Continuation of Ser. No. 561,285, March 24, 1975, abandoned.

[30] Foreign Application Priority Data

Mar. 22, 1974 Germany............................ 2413781

[52] U.S. Cl................................... 356/85; 356/244
[51] Int. Cl.²..................... G01J 3/30; G01N 21/16
[58] Field of Search....................... 356/85, 244, 246

[56] References Cited
UNITED STATES PATENTS

| | | | |
|---|---|---|---|
| 3,702,219 | 11/1972 | Braun et al. | 356/85 X |
| 3,778,156 | 12/1973 | Schmedes et al. | 356/85 X |

OTHER PUBLICATIONS

Massmann, Spectrochimica Acta, vol. 23B, No. 4, Apr. 1968 pp. 215–226.

Primary Examiner—John K. Corbin
Assistant Examiner—F. L. Evans
Attorney, Agent, or Firm—S. A. Giarratana; F. L. Masselle

[57] ABSTRACT

A heated graphite sample-atomizer for flameless atomic absorption spectroscopy in which a graphite sample tube is coaxially disposed within a pair of generally cylindrical electrode members which jointly envelope substantially the entire tube and define therewith a cylindrical flow passage for inert gas. The electrode members make electrical contact with respective ends of the tube to enable passage of a heating current therethrough. At least the outer end portions of the electrode members are telescoped within respective cooling jackets, the external cylindrical surfaces of the electrode members making a snug fit with complementary internal cylindrical surfaces of the cooling jackets at room temperature. The respective thermal expansion coefficients of the materials of the electrode members and cooling jackets are such as to create a press fit between the electrode members and cooling jackets under operating conditions.

6 Claims, 2 Drawing Figures

DEVICE FOR ATOMIZATION OF A SAMPLE

BACKGROUND OF THE INVENTION

This application is a continuation of application Ser. No. 561,285, filed Mar. 24, 1975 and now abandoned.

Field of the Invention

This invention relates to a device for flameless atomization of a sample for atomic absorption analysis and, more particularly, to such a device which comprises a tubular body in which the sample is contained and heated by means of an electric current passed through the body.

Summary of the Prior Art

Devices of the type to which the invention relates customarily employ a cylindrical graphite sample tube having a radial bore at substantially the midpoint of its length, the bore providing a port through which the sample may be introduced into the tube. The electrical heating current is passed through the tube by means of respective, generally annular, electrodes, typically also of graphite, in pressure contact with, and supporting, the tube ends. The annular configuration of the electrodes permits a beam of radiation, of selected spectral characteristics, to be directed through the tube to effect analysis of the atomized sample in a manner well known in the art of atomic absorption spectroscopy. In this connection, reference may be had to U.S. Pat. No. 2,847,899.

Normally, atomization of the sample requires heating of the tube (usually performed in stages to effect drying and ashing of the sample preparatory to its atomization) to extremely high temperatures; consequently, cooling jackets of high thermal conductivity material are provided for the electrodes and the tube is enveloped in a mantle of flowing protective gas to prevent its combustion. This requires defining an annular chamber for the gas surrounding the tube while still enabling access to the sample port.

The electrical current required for heating the tube is generally supplied to the electrodes by way of the cooling jackets which are of electrically conductive material and provided with suitable current leads. Consequently, both the electrical current path from the cooling jackets to the electrodes and the requirement for good heat conduction from the electrodes to the cooling jackets require a good electrical as well as thermal contact between the electrodes and the cooling jackets. In prior arrangements of this type such as shown in U.S. Pat. No. 3,778,156, conical mating surfaces are provided on the electrodes and the cooling jackets. The cooling jackets are mounted so as to be urged inwardly toward the electrodes which abut the respective ends of the graphite tube and are wedged into the cooling jackets.

It will be appreciated, particularly by reference to the aforementioned U.S. Pat. No. 3,778,156, as well as U.S. Pat. No. 3,788,752, that the quality of the contact between the mating surfaces is almost entirely dependent upon the accuracy with which such surfaces are fabricated. A relatively small deviation between the cone angles of mating surfaces will lead to a considerable diminution the area and intimacy of contact and, concomitantly, will result in higher resistance to both electrical and thermal conduction.

Another disadvantage of conical contact surfaces is the fact that they are not susceptible to a self-locking action. For example, in the case of the contact between a cooling jacket and the electrode, in operation the cooling jacket contracts relative to the electrode so that the mating conical surfaces generate an axial force component tending to push the electrode out of the cooling jacket against the counterforce applied by a spring or whatever means is employed to maintain the electrode position. In this connection, it should be noted that the friction coefficient of graphite, the material most frequently employed for the electrodes, is small and, consequently, is of scant assistance in resisting a force tending to expel the electrode from the cooling jacket.

SUMMARY OF THE INVENTION

It is an object of the present invention to provide a device of the type described above for flameless atomization of a sample in which thermal and electrical contact between cooling jackets and electrodes are facilitated and insured.

A further object is the provision of a device as characterized in the proceeding object in which electrodes are easily replaceable and extreme manufacturing tolerances are avoided.

To the accomplishment of the foregoing and other objects, the invention contemplates a device for flameless atomization of a sample for atomic absorption analysis comprising a hollow body of electrically conductive material defining a sample chamber having a radiation transmissive passage therethrough. Electrode means are in electrical contact with the hollow body at spaced locations for passing an electrical current through the body to cause resistive heating thereof. At least a portion of the electrode means has an external surface the cross-section of which is of constant configuration and dimension. Cooling jacket means are provided for the electrode means and includes an internal surface having a cross-section complementary to the cross-section of the external surface of the electrode means, the cross-sectional dimension of the internal surface being such in relation to the dimension of the cross-section of the external surface of the electrode means as to enable insertion of the electrode means into the cooling jacket means at room temperature and to cause an increase in contact pressure between the internal surface of the cooling jackets means and external surface of the electrode means due to differing thermal expansion of the electrode and cooling jacket means during operation of the device.

BRIEF DESCRIPTION OF THE DRAWINGS

An exemplary embodiment of the invention will now be described more fully with reference to the accompanying drawings in which.

DESCRIPTION OF THE PREFERRED EMBODIMENT

Figure 1:
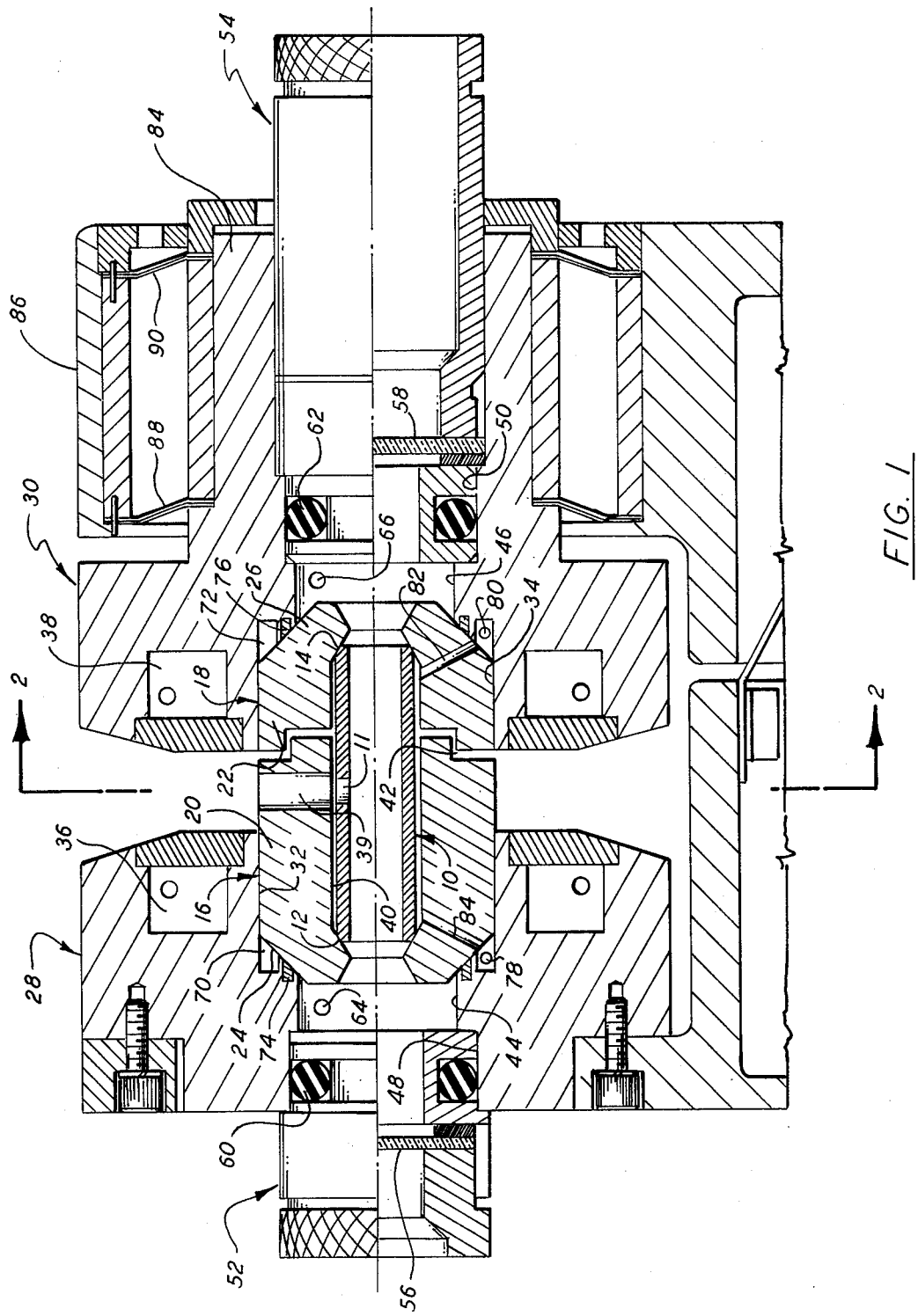
FIG. 1 is a longitudinal sectional view of a flameless atomization device according to the present invention taken along the axis of the sample tube and showing associated structure including electrodes and cooling jackets.

Referring now to the drawing and first in particular to FIG. 1, reference numeral 10 designates, in its entirety, a hollow body of electrically conductive material which defines a sample chamber and may herein be referred to as a sample tube. At substantially the mid-point of its length, tube 10 contains a radial bore 11 which provides a port for introducing the sample into the tube. As previously mentioned, tube 10, preferably, is fabricated of graphite and has conical end surfaces 12, 14, respectively. Respective electrode members 16, 18, comprise hollow cylindrical portions 20, 22, coaxially surrounding respective end portions of tubular body 10 and have annular end portions 24, 26, formed with internal conical surfaces complementary to and engaging end surfaces 12, 14, of tube 10.

Electrode members 16, 18, are mounted in respective cooling jackets 28, 30, each having a cylindrical recess 32, 34 for accommodation of the electrodes. Cooling jackets 28, 30, are fabricated of a material of high thermal and electrical conductivity and contain annular channels 36, 38, through which is circulated water or some other suitable coolant.

The outer cross-sectional dimension of cylindrical portions 20, 22, of electrode members 16, 18, is selected in relation to the internal cross-sectional dimension of recesses 32, 34, in cooling jacket 28, 30, so that, at room temperature, the electrode members fit snugly, i.e., can just be readily inserted into, the cooling jackets. In subsequent operation, when water or other coolant is circulated through channels 36 and 38, cooling the cooling jackets to below room temperature, they contract to create a positive contact pressure between the engaging cylindrical surfaces. The contact pressure is increased during operation as a result of the heating and concomitant expansion of the electrode members by conduction of heat from graphite tube 10. Thus, heating of the electrodes acts to improve the contact between the mating surfaces in the same sense and manner as differences in thermal coefficients of expansion.

The internal surface of the hollow cylindrical portion of electrode members 16, 18, coact with the external surface of graphite tube 10 to form an annular space 40. In this connection it will be noted that one of the electrodes, 16, is longer than the other and extends beyond the midpoint of the length of tube 10.

At a point coinciding with the midpoint of the length of tube 10, electrode member 16 contains a radial bore 39 in coaxial registration with, and of substantially larger diameter than, bore 11.

The confronting inner ends of electrode hollow cylindrical portions 20, 22, are stepped so as to form a stepped annular gap 42 which, due to the greater length of electrode 16, is axially offset from center (to the right as viewed in FIG. 1).

Coaxial with cylindrical recesses 32, 34, and disposed outwardly of the annular ends of electrode members 16, 18, cooling jackets 28, 30, have stepped counterbores therethrough comprising respective smaller diameter segments 44, 46, adjoining said recesses and, axially outwardly thereof, enlarged segments 48, 50.

Fitted into the counterbores of cooling jackets 28, 30, are hollow cylindrical inserts 52, 54 mounting respective radiation transparent windows 56, 58. Inserts 52, 54, are sealed in the counterbores by means of o-rings 60, 62, and can be axially withdrawn with the windows in place.

Figure 2:
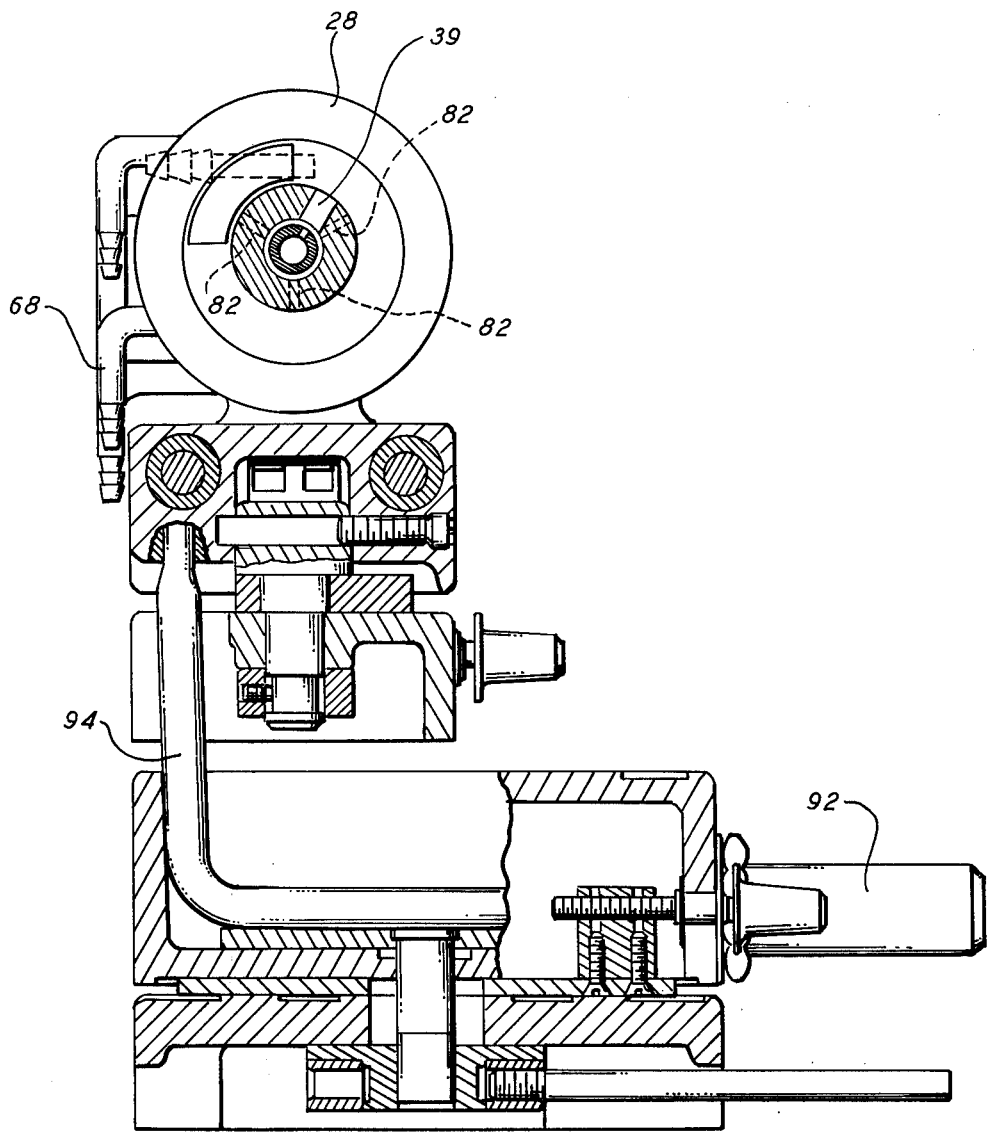
FIG. 2 is a section on line 2—2 of FIG. 1 looking in the direction of the arrows and including additional structure not present in FIG. 1.

Passages (not shown) in the cooling jackets for supplying protective gas open tangentially in the smaller diameter segments 44, 46, of the counterbores as indicated by ports 64, 66. The gas is supplied via a connection 68 shown in FIG. 2.

The external surfaces of annular end portions 24, 26 of electrode members 16, 18 are of conical configurations and coact with the walls of recesses 32, 34, to form annular spaces 70, 72 sealed with respect to counterbore segments 44, 46 by suitable packing strips 74, 76.

Additional protective gas passages (also not shown but in communication with gas connection 68, FIG. 2) extend tangentially into spaces 70, 72 as indicated by ports 78, 80. Spaces 70, 72 in turn are connected, by way of respective groups of three oblique ducts 82, 84 angularly-spaced at 120° intervals about the axis of tube 10 (as appears for ducts 82 in FIG. 2), with the ends of the annular space 40 surrounding the tube.

Cooling jacket 30 is spring-biased toward the adjoining end of tube 10 (i.e., to the left as viewed in FIG. 1). To this end, jacket 30 carries a cylindrical projection 84, coaxial with the tube 10 and the counterbore segments 46 and 50. Projection 84 is mounted in surrounding housing structure 86 by means of a pair of axially spaced spring washers, 88, 90, of the type sometimes referred to as castle springs or Belleville springs, which are oriented to provide spring bias in the desired direction, i.e., inwardly towards tube 10.

Cooling jackets 28, 30, are coupled to a source of electrical power by means of connection terminals such as 92 (FIG. 2) and a copper cable 94 so that a high current may be conducted through the cooling jackets, the cylindrical mating surfaces of the jackets and electrode members 16, 18 to tube 10.

It has been found to be advantageous to have the thermal expansion coefficient of the electrode material lower than that of the cooling jacket material.

From the foregoing, it will be appreciated that electrical and thermal contact between the electrode members and cooling jackets is accomplished without the conventional wedging action of conical mating surfaces. The cylindrical mating surfaces employed in accordance with the present invention are much easier to machine with the requisite accuracy. Moreover, they tend to be self-locking in operation.

The electrode members are dimensioned to be readily insertable into the cooling jackets at room temperature, as already explained. Introduction of coolant into the cooling jackets, reduces their temperature relative to the electrode members; as a result, the jackets contract to form a tight fit on the electrode members. During operation of the device, i.e., when the sample tube is heated, the tube expands and has the same effect, albeit in an opposite sense, of increasing the contact pressure between the mating surfaces of the electrode members and cooling jackets; this effect occurs, of course, even in the absence of coolant circulation in the cooling jackets and is additive where both heating of the tube and cooling of the jackets is taking place. Thus, the equivalent of a force fit may exist between the electrode members and cooling jackets during operation of the apparatus while still permitting easy disassembly at room temperatures.

What is claimed is:

1. A device for flameless atomization of a sample for atomic absorption analysis, comprising:
   a. a hollow body of electrically conductive material defining a sample chamber having a radiation-transmissive passage therethrough;
   b. electrode means in electrical contact with said body at spaced locations for passing an electrical current through the body to cause heating thereof, at least a portion of said electrode means having an external surface the cross-section of which is of constant configuration and dimension; and
   c. cooling jacket means for said electrode means including an internal surface having a cross-section complementary to the cross-section of the external surface of said electrode means, the cross-sectional dimension of said internal surface being such, in relation to the dimension of the cross-section of the external surface of said electrode means, as to enable insertion of the electrode means into said cooling jacket means at room temperature and to cause an increase in contact pressure between the internal surface of said cooling jacket means and external surface of said electrode means due to differing thermal expansion of the electrode and cooling jacket means during operation of the device.

2. A device according to claim 1 wherein said internal and external surfaces are of cylindrical configuration.

3. A device according to claim 1 wherein the thermal coefficient of expansion of the material of the electrode means is lower than that of the material of the cooling jacket material.

4. A device according to claim 1 wherein said body of electrically conductive material is of tubular configuration and said electrode means comprise a pair of electrodes having annular portions in contact with the ends of said tubular body.

5. A device according to claim 4 wherein said internal and external surface of the cooling jacket means and of said electrodes are of cylindrical configuration.

6. A device according to claim 5 wherein the thermal coefficient of expansion of the material of the electrode means is lower than that of the material of the cooling jacket material.

* * * * *